(12) United States Patent
Churchill et al.

(10) Patent No.: US 9,907,691 B2
(45) Date of Patent: Mar. 6, 2018

(54) INTRAUTERINE CONTRACEPTIVE DEVICES

(71) Applicant: HOLOGIC, INC., Marlborough, MA (US)

(72) Inventors: William Lucas Churchill, Bolton, MA (US); Victor Manuel Solano Umaña, Alajuela (CR)

(73) Assignee: HOLOGIC, INC., Marlborough, MA (US)

( * ) Notice: Subject to any disclaimer, the term of this patent is extended or adjusted under 35 U.S.C. 154(b) by 865 days.

(21) Appl. No.: 13/801,561

(22) Filed: Mar. 13, 2013

(65) Prior Publication Data
US 2014/0261444 A1    Sep. 18, 2014

(51) Int. Cl.
*A61F 6/14* (2006.01)
*A61K 33/34* (2006.01)

(52) U.S. Cl.
CPC ............. *A61F 6/144* (2013.01); *A61K 33/34* (2013.01)

(58) Field of Classification Search
CPC .... A61F 6/06; A61F 6/065; A61F 6/08; A61F 6/14; A61F 6/142; A61F 6/144; A61F 6/00; A61K 9/0039; A61K 9/0034
USPC ................. 128/830, 832, 833, 839
See application file for complete search history.

(56) References Cited

U.S. PATENT DOCUMENTS

| | | | |
|---|---|---|---|
| 3,559,641 A | 2/1971 | Lay | |
| 3,563,235 A | 2/1971 | Zipper | |
| 4,026,281 A | 5/1977 | Mayberry et al. | |
| 4,034,749 A | 7/1977 | Von Kesseru et al. | |
| 4,326,511 A | 4/1982 | Zimerman | |
| 4,351,326 A * | 9/1982 | Kosonen | 128/833 |
| 4,658,810 A | 4/1987 | Bauer | |
| 5,224,493 A | 7/1993 | Sawan et al. | |
| 5,660,848 A | 8/1997 | Moo-Young | |
| 6,711,925 B2 * | 3/2004 | Liao | 72/47 |
| 6,742,520 B1 * | 6/2004 | Wildemeersch | 128/830 |
| 8,118,028 B2 | 2/2012 | Karpati | |
| 2007/0075905 A1 * | 4/2007 | Denker et al. | 343/718 |
| 2012/0318276 A1 * | 12/2012 | Wildemeersch | 128/833 |

FOREIGN PATENT DOCUMENTS

| | | |
|---|---|---|
| WO | WO 96/01092 | 1/1996 |
| WO | 2012/063262 | 5/2012 |
| WO | 2012/147064 | 11/2012 |

* cited by examiner

*Primary Examiner* — Ophelia A Hawthorne
(74) *Attorney, Agent, or Firm* — Vista IP Law Group LLP

(57) ABSTRACT

A contraceptive intrauterine device having a support structure configured for transcervical implantation in a uterus, an active element coupled to the support structure, the active element having a core including copper that is at least partially coated with an outer layer including gold or gold alloy. A contraceptive intrauterine device having a support structure configured for transcervical implantation in a uterus, an active element coupled to the support structure, the active element including a copper core that is at least partially plated or coated with an outer layer including gold or gold alloy, wherein the copper core is configured to release copper ions after the device is implanted in a uterus, and wherein the gold or gold alloy outer layer is configured to control the release rate of copper ions release by the core. Methods for preventing conception by implanting said contraceptive intrauterine devices.

7 Claims, 4 Drawing Sheets

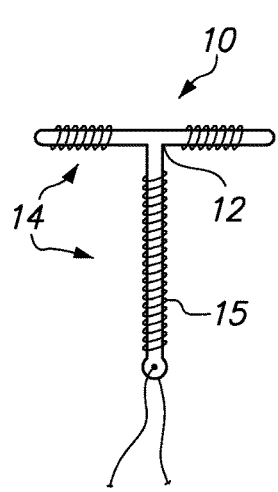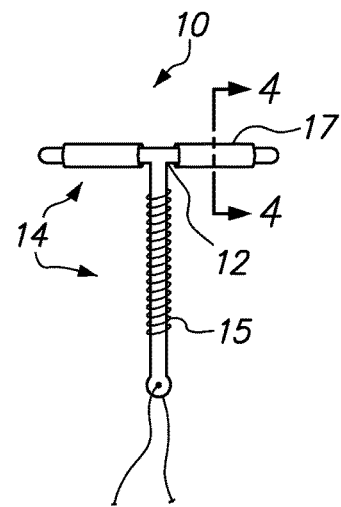
FIG. 1A  FIG. 1B
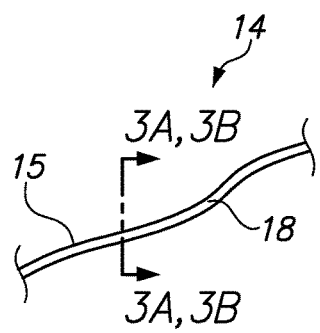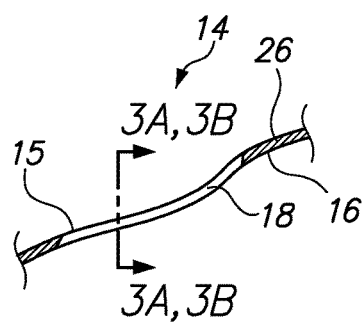
FIG. 2A  FIG. 2B
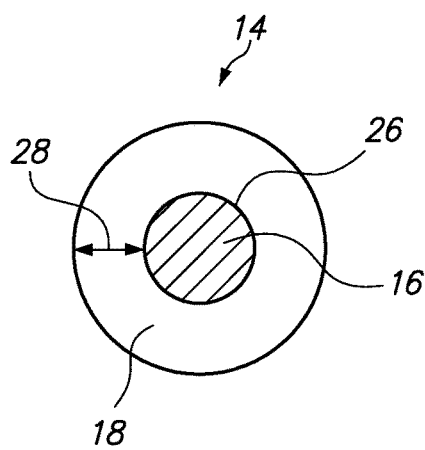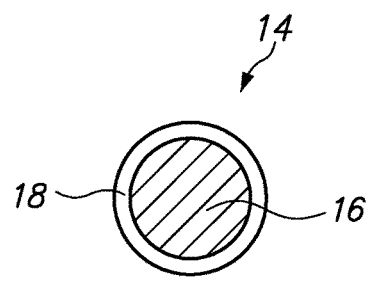
FIG. 3A  FIG. 3B

INTRAUTERINE CONTRACEPTIVE DEVICES

FIELD OF THE INVENTION

The present disclosure relates generally to contraceptive devices. More particularly, the present disclosure relates to copper intrauterine devices.

BACKGROUND

A variety of contraception methods are currently available; some require significant user involvement. While the effectiveness of existing contraceptives, including barrier methods and hormonal therapies, is well established, overcoming user non-compliance to improve overall efficacy has proven difficult.

A widely used contraception method that is less susceptible to user non-compliance are intrauterine devices (IUDs). IUDs have been found to have higher rates of reliability and are effective for a longer period of time than most other commercially available contraceptives. Additionally, the efficacy of IUDs made of copper or having copper as an active agent appear to be higher than non-metallic IUDs, and are effective for even longer periods of time (e.g. approximately 10 years). This type of IUD releases copper ions when in contact with intrauterine fluid and creates a hostile environment for conception. However, copper IUDs are associated with an increase in bleeding and cramping during the initial period of use. This initial release of copper ions is referred to as "burst release". Following the first few months of copper IUD implantation, users will experience normal cycles with the contraceptive advantages. Further, copper IUDs are also associated with severe corrosion and fragmentation of the copper in the IUD, as early as the first year of use. This copper fragmentation occurs even in commercially available IUDs having a support structure made of biocompatible, non-degradable material where a copper wire is wound around the support structure; the copper wire corrodes and breaks apart. Copper fragmentation may cause subsequent expulsion of fragmented parts of the IUD, increasing the risk of undesirable pregnancies, and reducing the effective period of use of the IUD.

Traditionally some copper IUDs are made with a wire of biocompatible, non-degradable materials having a thin coating of copper (U.S. Pat. No. 4,351,326). While this type of IUDs minimizes fragmentation by maintaining the structural integrity of the wire, the undesirable burst release of copper ions during the initial period after implantation may still occur. Further, the thin copper coating of the wire may substantially reduce the effective contraceptive period of the IUDs. More recently, some IUDs may include a copper alloy wire having a combination of metallic materials to increase the release of copper ions for a given surface area of copper, reduce bleeding and reduce infections after implantation (U.S. Pat. No. 8,118,028). However, the copper alloy wire having metals that increase the galvanic reaction of copper may accelerate its degradation and corrosion, therefore, reducing the effective period of use of the IUD. Additionally, the copper alloy may still be subject to undesirable fragmentation. Other IUDs may include a copper wire coated with a thin layer of degradable and bioabsorbable polymeric material to minimize the burst release of copper ions (WO 2012/063262). However, the polymeric layer degrades and is absorbed within the first few months of IUD implantation leaving the copper wire subject to corrosion and fragmentation that may reduce the effective period of use.

Therefore, there is an ongoing need to provide for more suitable copper IUDs that control the release rate of copper ions, particularly, during the initial period after implantation in a uterus, minimizing the undesirable side effects of the burst release of copper ions while maintaining the structural integrity and extending the contraceptive effective period of use of the IUD.

SUMMARY

In one embodiment of the disclosed inventions, a contraceptive intrauterine device comprises a support structure configured for transcervical implantation in a uterus, and an active element coupled to the support structure. The active element includes a core comprising copper that is at least partially coated with an outer layer comprising gold or gold alloy.

By way of non-limiting examples, the outer layer comprises an alloy that is at least about fifty weight percent gold. The outer layer has a thickness of about 2 to 100 micro centimeters, and more particularly, the outer layer may have a thickness of about 7 to 12 micro centimeters. The outer layer is plated on the copper core. The core comprises at least eighty five weight percent copper. The copper core has a surface area of about 200 to 1000 square millimeters.

In such embodiments, the active element is configured to release copper ions after implantation in a uterus at a release rate dependent on both a surface area of the copper core and a thickness of the outer layer. Additionally, the thickness of the outer layer is selected so that a release rate of copper ions during an initial period of use in a uterus is substantially less than a release rate that would occur in the absence of the outer layer. Further in such embodiments, the thickness of the outer layer is selected to decrease by at least about 50% a release rate of copper ions during an initial period of use in a uterus over a release rate that would occur in the absence of the outer layer.

Further in such embodiments, the support structure comprises a polymeric material. The active element comprises a wire wound around at least a portion of the support structure. The support structure may comprise a T-like, a V-like, a 7-like, a 8-like, a loop-like, a zigzag-like, or a ring-like configuration.

In another embodiment of the disclosed inventions, a contraceptive intrauterine device comprises a support structure configured for transcervical implantation in a uterus, and an active element coupled to the support structure. The active element comprises a copper core that is at least partially plated or coated with an outer layer comprising gold or gold alloy, wherein the copper core is configured to release copper ions after the device is implanted in a uterus, and wherein the gold or gold alloy outer layer is configured to control the release rate of copper ions release by the core.

By way of non-limiting examples, the outer layer has a thickness of about 7 to 12 micro centimeters. The copper core has a surface area of about 200 to 1000 square millimeters. A surface area of the copper core and a thickness of the gold or gold alloy outer layer are configured to control the rate of release of copper ions. The thickness of the outer layer is selected so that a release rate of copper ions during an initial period of use in a uterus is substantially less than a release rate that would occur in the absence of the outer layer.

In another embodiment of the disclosed inventions, a method for preventing conception comprises implanting a contraceptive intrauterine device in a uterus. The implanted contraceptive intrauterine device comprises a support structure configured for transcervical implantation in a uterus, and an active element coupled to the support structure, the active element including a core comprising copper that is at least partially coated with an outer layer comprising gold or gold alloy. By way of example, the implanted contraceptive intrauterine device releases copper ions in a uterus at a release rate during an initial period of use that is approximately equal to a release rate after the initial period of use.

Other and further aspects and features of embodiments of the disclosed inventions will become apparent from the ensuing detailed description in view of the accompanying figures.

BRIEF DESCRIPTION OF THE DRAWINGS

FIGS. 1A-B are perspective views of IUDs according to embodiments of the disclosed inventions;

FIGS. 2A-B is are perspective views of an active element according to embodiments of the disclosed inventions;

FIGS. 3A-B are cross-sectional views of an active element according to embodiments of the disclosed inventions;

DETAILED DESCRIPTION OF THE ILLUSTRATED EMBODIMENTS

Figure 4:
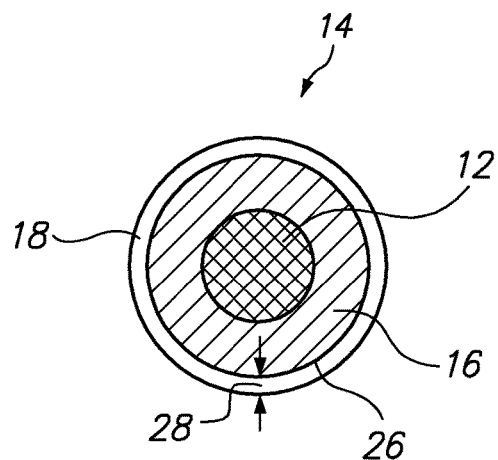
FIG. 4 is a cross-sectional view of an active element according to another embodiment of the disclosed inventions.
Figure 5A:
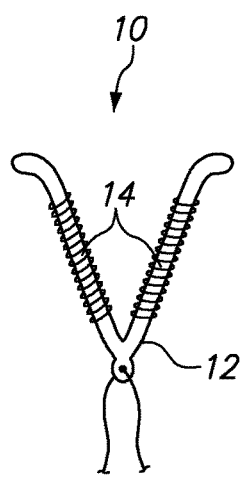
FIGS. 5A-F are perspective views of IUDs support structures according to embodiments of the disclosed inventions.
Figure 5B:
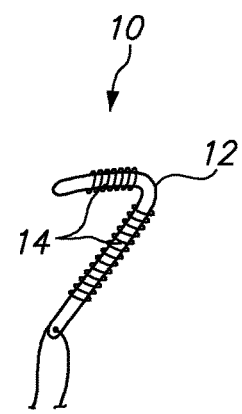
Figure 5C:
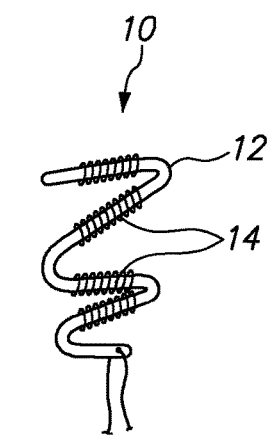
Figure 5D:
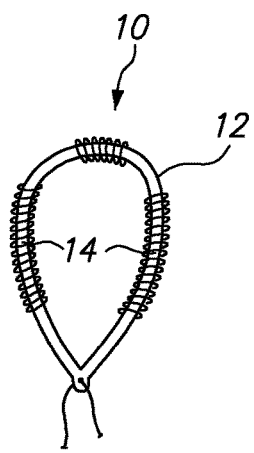
Figure 5E:
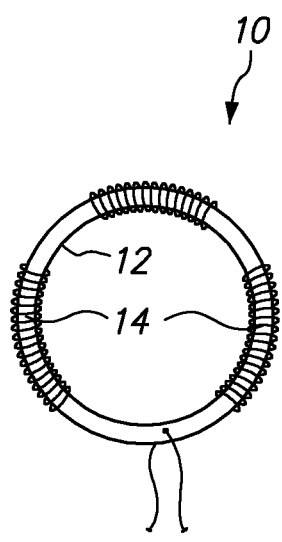
Figure 5F:
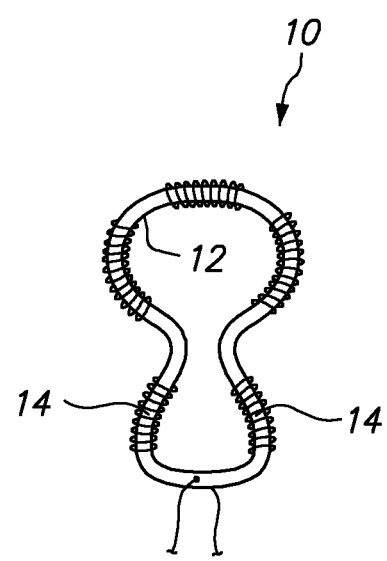

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIGS. 1A-B illustrate known types of support structures 12 for intrauterine devices 10 (IUD 10, IUDs 10) having a T-like configuration for transcervical implantation in a uterus. Other variations of the support structure 12 suitable for implantation in a uterus may be contemplated for the IUD 10, in which some exemplary configurations are depicted in FIGS. 5A-F. The support structure 12 may be made of polymeric materials, such as polyethylene, or other suitable biocompatible materials. As used in this specification, the term "support structure" may refer to any device or component to which one or more components may be directly or indirectly coupled, attached or secured.

The IUD 10 includes an active element 14 coupled to the support structure 12. Those skilled in the art will appreciate that various arrangements and configurations of the active element 14 and support structure 12 may be contemplated. By way of example, the active element 14 can have a variety of shapes including a wire, a tubular sleeve, or any other configuration adapted to be coupled to the support structure 12. In an exemplary arrangement, the IUD 10 may include one configuration of the active element 14, such as wire 15 wound around at least a portion of the support structure 12 (FIG. 1A). In another exemplary arrangement, IUD 10 may include a combination of a variety of configurations of the active element 14, such as wire 15 and sleeves 17; the sleeves 17 are disposed on sections of the support structure 12 (FIG. 1B).

Active Element

According to the disclosed inventions, the active element includes a core and an outer layer, where the core is at least partially coated on, plated with, or surrounded by the other layer. The core and the outer layer are made of biocompatible metallic materials. The core comprises copper (i.e. at least about eighty five weight percent copper), and the outer layer comprises gold or gold alloys (i.e. at least about fifty weight percent gold).

Copper is a degradable and biocompatible material that is known to be an effective contraceptive agent by releasing copper ions after implantation in a uterus that in contact with intrauterine fluid creates a hostile environment for conception. The release of copper ions in the initial period of use after implantation in a uterus (i.e. burst release) is substantially higher (e.g. 300-800 micrograms per day) than the amount of copper ions for contraceptive purposes, for example, 25-70 micrograms per day; other or different release rates may be contemplated for contraceptive purposes. The burst release of copper ions in a uterus is associated with increase of bleeding and cramping in users.

Gold is non-degradable, non-corrosive and biocompatible metallic material. IUDs having an active element including a copper core, at least partially coated with a gold or gold alloy outer layer, allows passage and release of copper ions in a uterus, and the outer layer further allows control of the release rate of copper ions in sufficient amounts for contraceptive purposes. The active element including a copper core at least partially coated with a gold or gold alloy outer layer is configured to control the release of copper ions, particularly, during the initial period of use in a uterus, minimizing the undesirable effects of the burst release of copper ions in a uterus. The controlled release rate of copper ions may dependent on a surface area of the copper core and a thickness of the gold or gold alloy outer layer. The thickness of the outer layer may be selected so that a release rate of copper ions during an initial period of use in a uterus is substantially less than a release rate that would occur in the absence of the outer layer. Further, the thickness of the outer layer may be selected to decrease by at least about 50% a release rate of copper ions during an initial period of use in a uterus over a release rate that would occur in the absence of the outer layer. The release rate of copper ions may be further regulated by the amount of surface area of the core that is coated with the outer layer of gold or gold alloy. For example, the release rate of copper ions may vary depending on the outer layer coverage of the core (i.e. from partial to substantial coverage of the core). A variety of measures and arrangements of the surface area of the copper core and the thickness of the gold or gold alloy outer layer may be contemplated for a controlled release of copper ions after implantation of the IUD in a uterus, particularly, during an initial period of use of the IUD in a uterus.

Commercially available IUDs have a copper surface area of about 400 square millimeters. According to the disclosed inventions, due to the gold and gold alloy outer layer, the copper core may have larger surface area that the current commercially available IUDs, since the outer layer controls the release rate of copper ions. A larger surface area of the copper core with the controlled release rate of copper ions by the outer layer is configured to extend the effective contraceptive period of IUDs. The copper core may have a surface area of about 200 to 1,000 square millimeters. The outer layer comprising gold or gold alloy may have a thickness of about 2 to 100 micro centimeters (approximately 1 to 40 micro inches). In one embodiment of the disclosed inventions, the outer layer has a thickness of about 7 to 12 micro centimeters (approximately 3 to 5 micro inches).

After implantation of copper IUDs in a uterus, copper degrades and corrodes allowing release of copper ions. The degradation and corrosion of copper occurs during the effective period of the IUDs, and the corrosion of copper may also be severe within the initial year of the IUD use. The corrosion and degradation may cause fragmentation of the copper and subsequent expulsion of fragmented parts of the IUD reducing the effective contraceptive period of use of the IUD. The active element having a copper core at least partially coated with gold or gold alloy outer layer is further configured to maintain the structural integrity of the active element in an IUD. Despite the degradation and corrosion of the copper core, the non-degradable gold or gold alloy outer layer is adapted to maintain the configuration and shape of the active element preventing expulsion of fragmented copper elements and further extending contraceptive effective period of the IUD. By way of example, the embodiment of FIG. 2A depicts an active element 14 having a wire 15 configuration, where the copper core is coated with the gold or gold alloy outer layer 18. The gold or gold alloy outer layer 18 may be adapted to encase the copper core, like a pipe, maintaining the structural integrity of the wire configuration of the active element 14, regardless of the corrosion of the copper core over time.

FIGS. 2A-B illustrate a wire 15 (an example of the active element 14) in accordance with embodiments of the disclosed inventions. FIG. 2A illustrates a perspective section of the active element 14 having a wire 15 configuration. A core (not shown) comprising copper is substantially coated with an outer layer 18 comprising gold or gold alloy. FIG. 2B illustrate another perspective section of the active element 14 having a wire 15 configuration. The copper core 16 is partially coated with a gold or gold alloy outer layer 18. The copper core 16 has a surface area 26.

FIGS. 3A and 3B illustrate cross-sectional views of the wire 15 of either of FIGS. 2A and 2B. The copper core 16 has a surface area 26. The gold or gold alloy outer layer 18 has a thickness 28 of about 2 to 100 micro centimeters. The thickness 28 of the outer layer 18 may varied within the referred range. In one embodiment of the disclosed inventions, the thickness 28 is about 7 to 12 micro centimeters (FIG. 3B). The thickness 28 of the outer layer 18 illustrated in FIGS. 3A-B are not necessarily drawn to scale. As disclosed above, a variety of measures and arrangements of the surface area 26 of the copper core 16 and the thickness 28 of the gold or gold alloy outer layer 18 may be contemplated for a controlled release of copper ions after implantation of the IUD 10, particularly, during an initial period of use of IUD 10 in a uterus. For example, the release rate of copper ions by the active element 14 after implantation of the IUD 10 in a uterus (e.g. during an initial period of use) may depend on both, the surface area 26 of the core 16 and, the thickness 28 of the outer layer 18. The thickness of the outer layer may be selected so that the release rate of copper ions during the initial period of use in a uterus is substantially less than a release rate that would occur in the absence of the outer layer. Further, the thickness of the outer layer may be selected to decrease by at least about 50% the release rate of copper ions during the initial period of use in a uterus over a release rate that would occur in the absence of the outer layer. The release rate of copper ions may be further regulated by the surface area 26 of the core 16 that is coated with the outer layer 18 of gold or gold alloy. For example, the release rate of copper ions may vary depending on the amount of outer layer 18 coverage of the surface area 26 (i.e. from partial to substantial coverage of the core). Further, the active element 14 may be configured to release copper ions after implantation of the IUD 10 in a uterus, where the surface area 26 of the copper core 16 and the thickness 28 of the gold or gold alloy outer layer 18 are configured to control the release rate of copper ions during an initial period of use of IUD 10 in a uterus.

FIG. 4 illustrate a cross-sectional view of sleeve 17 (an example of the active element 14) in accordance with embodiments of the disclosed inventions. The sleeve 17 is disposed on the support structure 12; the sleeve further has a copper core 16 having a surface area 26 and a gold or gold alloy outer layer 18 having a thickness 28.

FIGS. 5A-F illustrate various support structures 12 of IUDs 10 in accordance with embodiments of the disclosed inventions. The support structure 12 includes a V-like, a 7-like, a zigzag-like, a loop-like, a ring-like and 8-like configurations. Other variations of support structure 12 suitable for implantation in a uterus may be contemplated for the IUD 10.

Experimental Data

Figure 6:
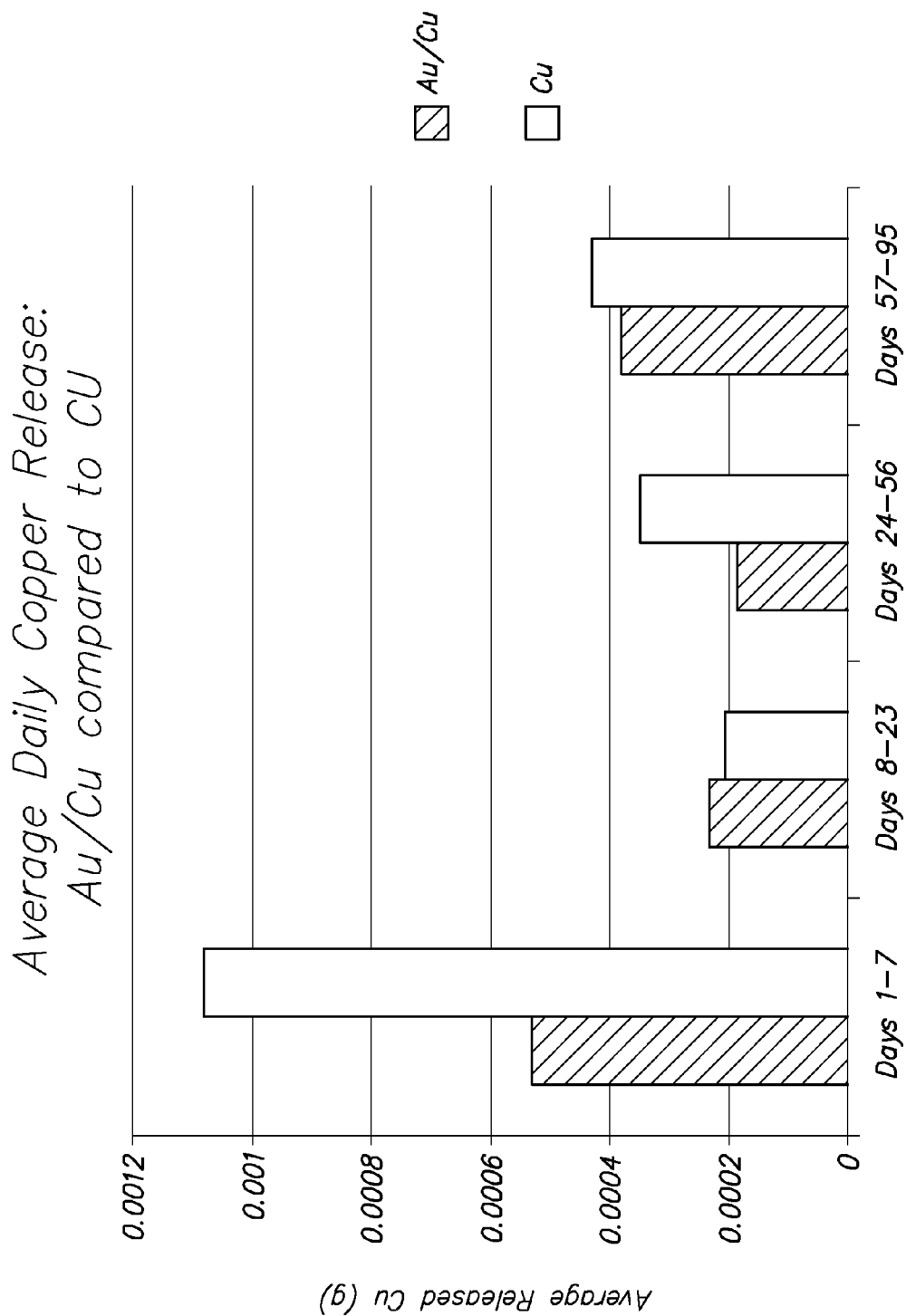
FIG. 6 is an experimental data table according to embodiments of the disclosed inventions.

In accordance with the disclosed inventions, experiments were conducted on copper wires samples (i.e. 14 grams) plated with gold (i.e. 3 to 5 micro inches of 98% gold). Samples of gold plated copper wires (Au/Cu) and control copper wires (Cu) were separately immerse in 200 milliliters of simulated uterine fluid (SUF) with a pH of 7.0 at 37° C. over time (up to 95 days). The variations of copper ions release on Au/Cu and Cu samples are shown on FIG. 6.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the scope of the present inventions as defined by the claims.

What is claimed is:

1. A contraceptive intrauterine device, comprising:
a support structure configured for transcervical implantation in a uterus,
an active element coupled to the support structure, the active element comprising a copper core that is at least partially plated or coated with an outer layer comprising gold or gold alloy, wherein the copper core is configured to release copper ions after the device is implanted in a uterus, and wherein the gold or gold alloy outer layer is configured to control the release rate of copper ions release by the core.

2. The contraceptive intrauterine device of claim 1, wherein the outer layer has a thickness of about 7 to 12 micro centimeters.

3. The contraceptive intrauterine device of claim 1, wherein the copper core has a surface area of about 200 to 1000 square millimeters.

4. The contraceptive intrauterine device of claim 1, wherein a thickness of the outer layer is selected so that a release rate of copper ions during an initial period of use in a uterus is substantially less than a release rate that would occur in the absence of the outer layer.

5. A contraceptive intrauterine device, comprising:
a support structure configured for transcervical implantation in a uterus,
an active element coupled to the support structure, the active element including a core comprising copper that is at least partially coated with an outer layer comprising gold or gold alloy, wherein the active element is configured to release copper ions after implantation in a uterus at a release rate dependent on both a surface area of the copper core and a thickness of the outer layer.

6. The contraceptive intrauterine device of claim 5, wherein the thickness of the outer layer is selected so that a release rate of copper ions during an initial period of use in a uterus is substantially less than a release rate that would occur in the absence of the outer layer.

7. The contraceptive intrauterine device of claim 5, wherein the thickness of the outer layer is selected to decrease by at least about 50% a release rate of copper ions during an initial period of use in a uterus over a release rate that would occur in the absence of the outer layer.

* * * * *